(12) United States Patent
Murphy et al.

(10) Patent No.: US 11,129,382 B2
(45) Date of Patent: Sep. 28, 2021

(54) METHODS AND DISINFECTING COVERS FOR USE IN DISINFECTING RESILIENT MEDICAL PATIENT PRESSURE REDISTRIBUTION SUPPORTS

(71) Applicant: KICKBALL CONCEPTS LLC, Sterling, VA (US)

(72) Inventors: Harrison R. Murphy, Sterling, VA (US); Juraj Michal Daniel Slavik, II, McLean, VA (US)

(73) Assignee: kickball concepts llc, Sterling, VA (US)

( * ) Notice: Subject to any disclaimer, the term of this patent is extended or adjusted under 35 U.S.C. 154(b) by 239 days.

(21) Appl. No.: 14/920,559

(22) Filed: Oct. 22, 2015

(65) Prior Publication Data

US 2016/0037769 A1 Feb. 11, 2016
US 2017/0135341 A9 May 18, 2017

Related U.S. Application Data

(63) Continuation of application No. PCT/US2014/035139, filed on Apr. 23, 2014.
(Continued)

(51) Int. Cl.
*A01N 25/34* (2006.01)
*A61L 2/23* (2006.01)
(Continued)

(52) U.S. Cl.
CPC ............ *A01N 25/34* (2013.01); *A47C 31/007* (2013.01); *A61G 7/0502* (2013.01);
(Continued)

(58) Field of Classification Search
CPC ..... A47C 31/007; A47C 31/10; A47C 31/105; A47C 31/11; A47C 31/113; A47C 31/116;
(Continued)

(56) References Cited

U.S. PATENT DOCUMENTS 3,344,444 A  10/1967  McNeal
3,946,450 A  3/1976  Staggs
(Continued)

FOREIGN PATENT DOCUMENTS

EP  0963760 A1 * 12/1999  ............. C08L 77/00
EP  0964026 A1 * 12/1999  ............. B32B 27/22
(Continued)

OTHER PUBLICATIONS

HomeDashWizardDotCom, Mattress Care, May 5, 2011, YouTube, https://www.youtube.com/watch?v=Hs4DMxejyqw (Year: 2011).*
(Continued)

*Primary Examiner* — Nicholas F Polito
(74) *Attorney, Agent, or Firm* — Heslin Rothenberg Farley & Mesiti P.C.

(57) ABSTRACT

A disinfecting cover for use in disinfecting a weight bearing upper surface of a resilient medical patient pressure redistribution support includes a thin barrier membrane drapable on top of the weight bearing upper surface of the resilient support, and a peripherally-extending edge terminating between the peripherally-extending side of the resilient support between the weight bearing upper surface and the bottom surface of the support. The thin barrier membrane comprises an anti-microbial disinfectant, and being non-fibrous, and impervious to the transfer of fluid from the first main surface to the second main surface. The thin barrier membrane comprises a thickness operable to maintain the weight distribution of a patient on the weight bearing upper surface of the resilient medical patient pressure redistribution support substantially the same compared to the weight distribution without the thin barrier membrane.

37 Claims, 7 Drawing Sheets

Related U.S. Application Data

(60) Provisional application No. 61/815,089, filed on Apr. 23, 2013.

(51) Int. Cl.
    *A61G 7/05*     (2006.01)
    *A47C 31/00*     (2006.01)
    *A61G 7/057*     (2006.01)

(52) U.S. Cl.
    CPC ............ *A61G 7/05715* (2013.01); *A61L 2/23* (2013.01); *A61G 2203/76* (2013.01)

(58) Field of Classification Search
    CPC .... A61G 1/01; A61G 7/0502; A61G 7/05715; A61G 2203/76; A47G 2009/001; A47G 9/0246; A01N 25/34; A61L 2/23
    See application file for complete search history.

(56) References Cited

U.S. PATENT DOCUMENTS

| | | | |
|---|---|---|---|
| 6,631,529 B1 | 10/2003 | Erickson | |
| 6,649,236 B2 | 11/2003 | Haskin | |
| 7,635,809 B2 | 12/2009 | Higgs et al. | |
| 7,682,994 B2 | 3/2010 | Van Emden et al. | |
| 7,939,149 B2 | 5/2011 | Haskin et al. | |
| 2002/0148047 A1* | 10/2002 | Corzani | A47C 27/006 |
| | | | 5/738 |
| 2003/0049294 A1* | 3/2003 | Porchia | A01M 29/12 |
| | | | 424/405 |
| 2003/0121101 A1 | 7/2003 | Corzani et al. | |
| 2003/0172458 A1* | 9/2003 | Bonfanti | A47G 9/007 |
| | | | 5/490 |
| 2005/0129937 A1* | 6/2005 | Patton | A01N 25/34 |
| | | | 428/354 |
| 2005/0132498 A1 | 6/2005 | Vrionis | |
| 2008/0299163 A1 | 12/2008 | Haskin et al. | |
| 2009/0144900 A1 | 6/2009 | Marrache | |
| 2011/0005000 A1 | 1/2011 | Rippe et al. | |

FOREIGN PATENT DOCUMENTS

| | | | | |
|---|---|---|---|---|
| WO | WO 1985/02526 A1 | 6/1985 | | |
| WO | WO-2004087226 A1 * | 10/2004 | ............... | C08L 79/00 |
| WO | WO-2007125376 A1 * | 11/2007 | ......... | A61G 7/05715 |
| WO | WO 2014/176331 A1 | 10/2014 | | |

OTHER PUBLICATIONS

International Search Report and Written Opinion of the International Searching Authority, PCT/US2014/035139, published as WO 2014/176331, 12-pages, dated Sep. 5, 2014.

Sheila Shahidi and Jakub Wiener, "Antibacterial Agents in Textile Industry", Antimicrobial Agents, Dr. Varaprasad Bobbarala (Ed.), Chapter 19, INTECH Open Access Publisher, pp. 387-406, 2012.

* cited by examiner

800

```
┌─────────────────────────────────────┐
│ PROVIDING A DISINFECTING COVER      │
│ HAVING A FIRST MAIN SURFACE, AN     │─ 810
│ OPPOSITE SECOND MAIN SURFACE,       │
│ AND A PERIPHERALLY-EXTENDING EDGE,  │
│ THE DISINFECTING COVER BEING        │
│ NON-FIBROUS COMPRISING AN           │
│ ANTI-MICROBIAL DISINFECTANT         │
└─────────────────────────────────────┘
```

DRAPING THE FIRST MAIN SURFACE OF THE DISINFECTING COVER OVER THE WEIGHT BEARING UPPER SURFACE OF THE RESILIENT MEDICAL PATIENT PRESSURE REDISTRIBUTION SUPPORT WITH PORTIONS OF THE FIRST MAIN SURFACE, THE OPPOSITE SECOND MAIN SURFACE, AND THE PERIPHERALLY-EXTENDING EDGE OF THE DISINFECTING COVER EXTENDING AWAY FROM THE WEIGHT BEARING UPPER SURFACE — 820

POSITIONING THE PORTIONS OF THE FIRST MAIN SURFACE, THE OPPOSITE SECOND MAIN SURFACE, AND THE PERIPHERALLY-EXTENDING EDGE EXTENDING AWAY FROM THE WEIGHT BEARING UPPER SURFACE BELOW THE UPPER WEIGHT-BEARING SURFACE OF THE RESILIENT MEDICAL PATIENT PRESSURE REDISTRIBUTION SUPPORT AND OVER A PORTION OF THE PERIPHERALLY-EXTENDING SIDE OF THE RESILIENT MEDICAL PATIENT PRESSURE REDISTRIBUTION SUPPORT WITH THE PERIPHERALLY-EXTENDING EDGE OF THE PLANAR DISINFECTING COVER DISPOSED ABOVE THE LOWER SURFACE OF RESILIENT MEDICAL PATIENT PRESSURE REDISTRIBUTION SUPPORT — 830

RELEASABLY SECURING THE DISINFECTING COVER IN POSITION OVER THE WEIGHT BEARING UPPER SURFACE AND ALONG THE PERIPHERALLY-EXTENDING SIDE OF THE RESILIENT MEDICAL PATIENT PRESSURE REDISTRIBUTION SUPPORT — 840

Fig. 15

METHODS AND DISINFECTING COVERS FOR USE IN DISINFECTING RESILIENT MEDICAL PATIENT PRESSURE REDISTRIBUTION SUPPORTS

CLAIM TO PRIORITY

This application is a continuation of International Application PCT/US2014/035139, filed Apr. 23, 2014, and published under the PCT Articles in English as WO 2014/176331 on Oct. 30, 2014, which International Application claims the benefit of U.S. Provisional Patent Application No. 61/815,089, filed Apr. 23, 2013, entitled "Methods, Systems, And Materials For Surface Disinfection", the entire contents of these applications being hereby incorporated herein by reference.

FIELD OF THE DISCLOSURE

The present disclosure relates to generally to disinfection of medical supports, and more particularly to methods and disinfecting covers for use in disinfecting resilient medical patient pressure redistribution supports.

BACKGROUND OF THE DISCLOSURE

Institutional infection control measures and the associated need for efficacious disinfection of patient contact surfaces in healthcare settings has drawn increased attention from healthcare providers and regulatory bodies as the rates of healthcare-associated infections (HAI) and resultant deaths has increased.

U.S. Pat. No. 6,649,236, issued to Haskin, discloses an anti-fomitic device in the form of a bag or envelope that forms a cover for an object for preventing cross-infection by bacteria and other pathogens that may reside on the object. The anti-fomitic device is a flat, flexible bag or envelope with a closure mechanism at one or both ends of the bag or envelope, having a sterile interior that is sealed during manufacture to maintain sterility. Therefore, no outer wrapping for the anti-fomitic device is required. The anti-fomitic device is inverted when used to cover the object and results in an ultimate outer surface that is initially sterile. Materials for the coverings/bags serve as a barrier to the transmission of pathogens.

U.S. Pat. No. 7,939,149, issued to Haskin et al., discloses a heat-shrinkable anti-fomitic device incorporating anti-microbial metal wherein the device, in the form of a bag or tube, forms a cover for an object, preventing cross-infection by bacteria and other pathogens that may reside on the object. Anti-microbial metal ions from the cover further reduce future cross-infection from the object by killing pathogens. The anti-microbial, heat-shrinkable, anti-fomitic device can have a sterile interior that is sealed or stored flat during manufacture to maintain sterility. Therefore, no outer wrapping for the anti-fomitic device is required. The anti-fomitic device can be inverted when used to cover the object to present an outer surface that is initially sterile. A plurality of such devices can be heat shrunk to an object such that removal of the outer layer will further prevent cross contamination. Heat shrink film materials for the coverings/bags serve as a barrier to the transmission of pathogens and conform closely to the covered object.

U.S. Patent Application Publication No. 2008/0299163, by Haskin et al., discloses an anti-fomitic device in the form of a bag or envelope forms a cover for an object for preventing cross-infection by bacteria and other pathogens that may reside on the object. The anti-fomitic device is a flat, flexible bag or envelope with a closure mechanism at one or both ends of the bag or envelope, having a sterile interior that is sealed during manufacture to maintain sterility. Therefore, no outer wrapping for the anti-fomitic device is required. The anti-fomitic device is inverted when used to cover the object and results in an ultimate outer surface that is initially sterile. Materials for the coverings/bags serve as a barrier to the transmission of pathogens.

Another approach includes integrating or coating anti-microbial agents into healthcare fabrics using traditional methodologies, for example, where a chemical compound or liquid is added to the coating medium (e.g. polyurethane or rubber).

Other approaches for attempting to control microbial pathogens on specialized medical patient support surfaces employ an additional, removable and launderable fabric cover to the outside of the support surface.

There is a need for further methods and disinfecting covers for use in disinfecting resilient medical patient pressure redistribution supports.

SUMMARY OF THE DISCLOSURE

In a first aspect, the present disclosure provides a method for disinfecting a weight bearing upper surface of a resilient medical patient pressure redistribution support in which the resilient medical patient pressure redistribution support includes a lower surface, and a peripherally-extending side disposed between the weight bearing upper surface and the lower surface. The method includes providing a disinfecting cover having a first main surface, an opposite second main surface, and a peripherally-extending edge, the disinfecting cover being non-fibrous and comprising an anti-microbial disinfectant, and draping the first main surface of the disinfecting cover over the weight bearing upper surface of the resilient medical patient pressure redistribution support with portions of the first main surface, the opposite second main surface, and the peripherally-extending edge of the disinfecting cover extending away from the weight bearing upper surface. Portions of the first main surface, the opposite second main surface, and the peripherally-extending edge extending away from the weight bearing upper surface is positioned below the weight bearing upper surface of the resilient medical patient pressure redistribution support and over a portion of the peripherally-extending side of the resilient medical patient pressure redistribution support with the peripherally-extending edge of the planar disinfecting cover disposed above the lower surface of resilient medical patient pressure redistribution support. The disinfecting cover is releasably secured in position over the weight bearing upper surface and along the peripherally-extending side of the resilient medical patient pressure redistribution support. The disinfecting cover comprises a thickness operable to maintain the weight distribution of a patient on the weight bearing upper surface of the resilient medical patient pressure redistribution support substantially the same compared to the weight distribution of the patient on the weight bearing upper surface of the resilient medical patient pressure redistribution support without the disinfecting cover.

In a second aspect, the present disclosure provides a disinfecting cover for use in disinfecting a weight bearing upper surface of a resilient medical patient pressure redistribution support in which the resilient medical patient pressure redistribution support includes the weight bearing upper surface, a bottom surface, and a peripherally-extending side disposed and extending between the weight bearing upper surface and the bottom surface. The disinfecting cover comprising a thin barrier membrane having a first main surface, an opposite second main surface, and a peripherally-extending and surrounding edge disposed between the first main surface and the opposite second main surface. The first main surface and the opposite second main surface of the thin barrier membrane operably sized and configured so that the first main surface is drapable on top of the weight bearing upper surface of the resilient medical patient pressure redistribution support, and the peripherally-extending edge terminating between the peripherally-extending side of the resilient medical patient pressure redistribution support between the weight bearing upper surface and the bottom surface of the resilient medical patient pressure redistribution support. The thin barrier membrane comprises an anti-microbial disinfectant, and is non-fibrous and impervious to the transfer of fluid from the first main surface to the second main surface. The thin barrier membrane comprises a thickness operable to maintain the weight distribution of a patient on the weight-bearing surface of a resilient medical patient pressure redistribution support substantially the same compared to the weight distribution of the patient on the weight-bearing surface of a resilient medical patient pressure redistribution support without the thin barrier membrane.

BRIEF DESCRIPTION OF THE DRAWINGS

The subject matter of the disclosure is particularly pointed out and distinctly claimed in the concluding portion of the specification. The disclosure, however, may best be understood by reference to the following detailed description of various embodiments and the accompanying drawings in which:

FIG. 15 is a flowchart of one embodiment for a method for disinfecting a weight bearing upper surface of a resilient medical patient pressure redistribution support in accordance with aspects of the present invention.

DETAILED DESCRIPTION OF THE DISCLOSURE

Figure 1:
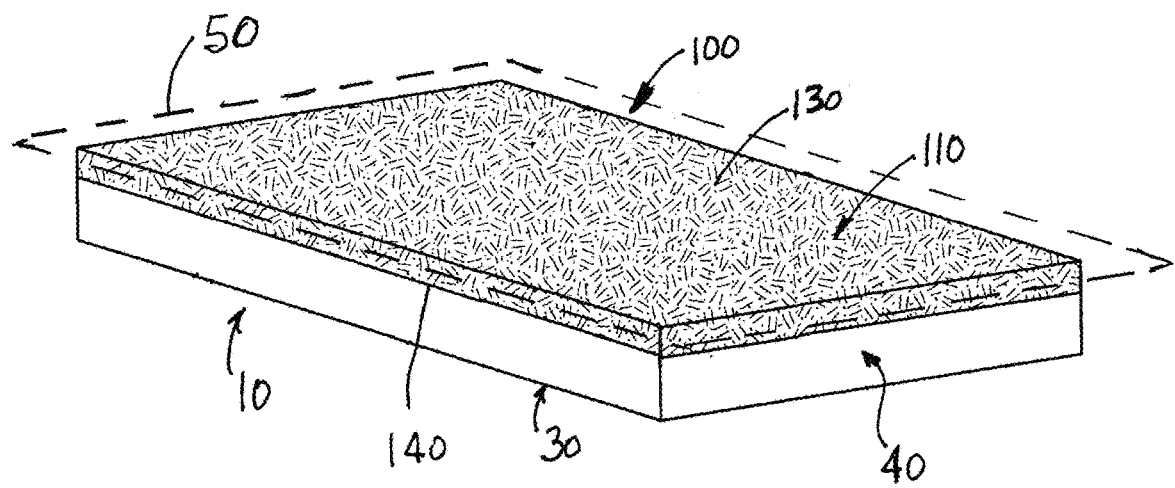
FIG. 1 is an isometric view of one embodiment of a disinfecting cover disposed on a resilient medical patient pressure redistribution support in accordance with aspects of the present disclosure.

The present disclosure relates generally to methods, systems, and materials for disinfection of specialized medical patient support surfaces such as in connection with devices that may be delivered in-place during patient use or, alternatively, while the surfaces are not in use by patients.

The methods, systems and materials may relate to the in-place, disinfection of specialized medical patient support surfaces through use of, in one embodiment, a uniform, non-liquid and non-fibrous, polymer based planar media. The media may simultaneously offer the desirable attributes of providing resistance to blood-borne pathogen and viral penetration, contact inhibition control of life-threatening bacterial and fungal organisms and de minimus influence on the engineered therapeutic benefits of controlled force per unit area exerted perpendicularly to the planar surface of such surfaces.

It has been discovered that a method for disinfecting the exterior fabric cover of a specialized medical patient support surface device using a substantially uniform, non-liquid and non-fibrous polymer based media that is manufactured with anti-microbial technologies wherein the substantially uniform, non-liquid and non-fibrous polymer based media when disposed atop a specialized medical patient support surface concurrent with patient use of the surface or while surface is not in use by patient may be efficacious in the killing of a number of pathogens associated with causing healthcare-associated infections (HAI) and can do so without adversely affecting the interface pressure management design and performance of the support surface.

Additionally, the present disclosure of using a substantially uniform, non-liquid and non-fibrous polymer based media to provide a method of in-place disinfection that can also provide an added shielding layer of pathogen and fluid impermeable protection to a specialized medical patient support device in the event that the designed integrity of original cover material of the specialized medical patient support device has become breached, penetrated or otherwise compromise through use, wherein the breach, penetration or compromise may or may not be visible or evident to the user, custodian or owner of such device.

Furthermore, the present disclosure of using a substantially uniform, non-liquid and non-fibrous polymer based media may also be able to deliver desirable, ancillary benefits through moisture vapor transmission control and resistance to the passage of blood, bodily fluids or blood- or bodily fluid-borne pathogens as measured by test protocols cited herein.

The substantially uniform, non-liquid and non-fibrous polymer based media may be manufactured with anti-microbial technologies such as in an embodiment being non-absorbent and free of fibrous materials.

The present disclosure will be described more fully hereinafter and with reference to the accompanying drawings, which show exemplary and non-limiting embodiments of the disclosure. This disclosure may, however, be embodied in many different forms and should not be construed as limited to the embodiments set forth herein.

Reference is now provided to the accompanying drawings which are not drawn to scale and are intended to provide a non-limiting visual representation of a method of disinfection for specialized medical patient surfaces that may be delivered in-place during patient use or, alternatively, while the surfaces are not in use by patients.

Figure 2:
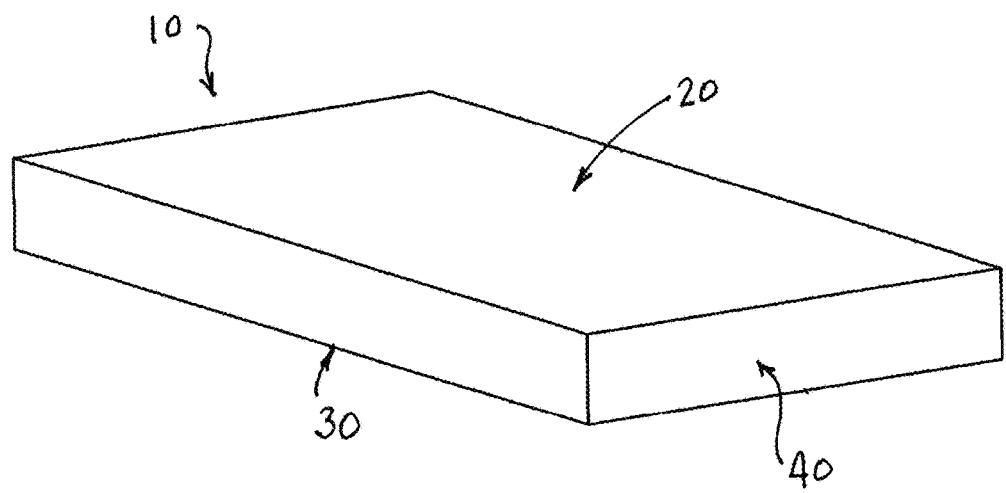
FIG. 2 is an isometric view of the resilient medical patient pressure redistribution support of FIG. 1.

FIG. 1 illustrated a disinfecting media or cover 100 that may be readily and easily placed on or draped onto a resilient medical patient pressure redistribution support 10 in accordance with aspects of the present disclosure. For example, disinfecting media or cover 100 may be operable for use in disinfecting a weight bearing upper surface 20 (FIG. 2) of resilient medical patient pressure redistribution support 10. As shown in FIG. 2, resilient medical patient pressure redistribution support 10 may include weight bearing upper surface 20, a bottom surface 30, and a peripherally-extending side 40 disposed and extending between the weight bearing upper surface and the bottom surface. As described below, the disinfecting media or cover may be releasably secured to the resilient medical patient pressure redistribution support such at least portions of the disinfecting media or cover are directly attached to the resilient medical patient pressure redistribution support so that the movement of the disinfecting media or cover relative to the resilient medical patient pressure redistribution support is inhibited.

In one embodiment, the resilient medical patient pressure redistribution support may be generally a rectangular cuboid or prism, for example a mattress, wherein the upper planar rectangular surface is the surface onto which a patient may lie. The upper planar rectangular surface may also be referred to as a "panel" and is intended in a one-sided support surface construction to be the side used by patients or persons sleeping or reposing on the support surface. The vertical sides or the side border may define a head or foot "border." The opposing faces of sides of the support may be typically of equal dimensions and shape. Typically, the opposing face to the upper surface is a bottom face or surface of the mattress. For supports to be flappable, the upper and bottom surfaces are substantially similar.

Some more complex designs for specialized medical patient support surfaces may depart from the rectangular cuboid shape provided herein and may add raised edges, depressions or other surface modifications for certain therapeutic considerations. The present disclosure contemplates such design departures and is not intended to be limited by such modifications.

Figure 3:
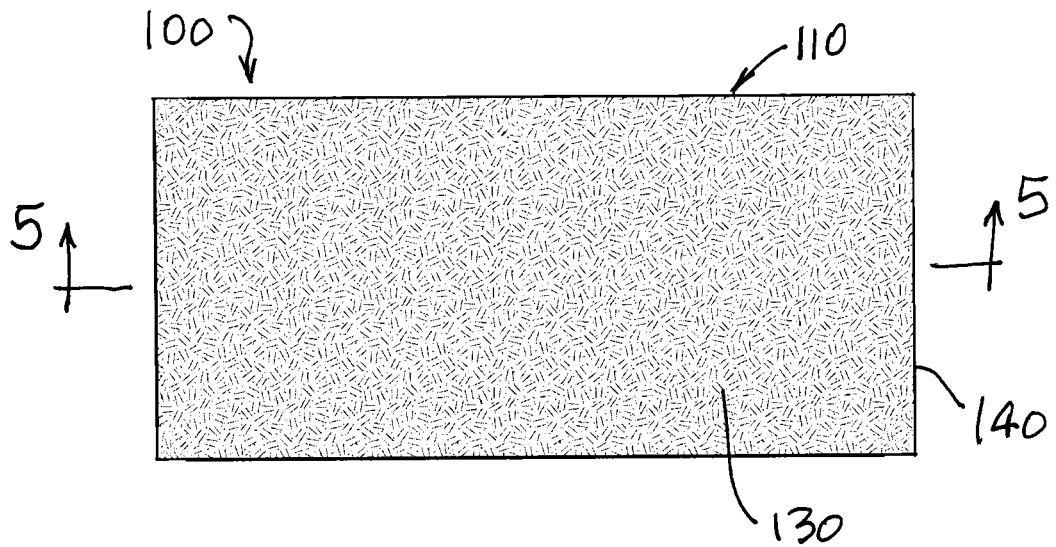
FIGS. 3 and 4 are a top view and a bottom view, respectively, of the disinfecting cover of FIG. 1.
Figure 4:
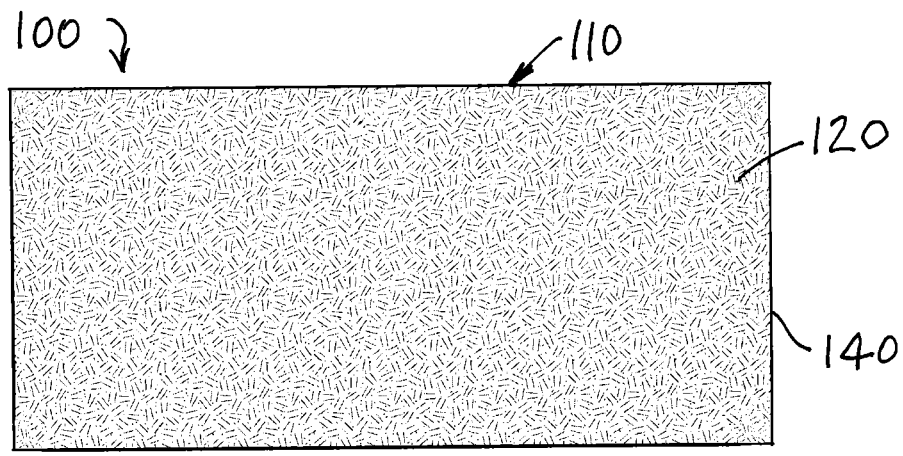
Figure 5:
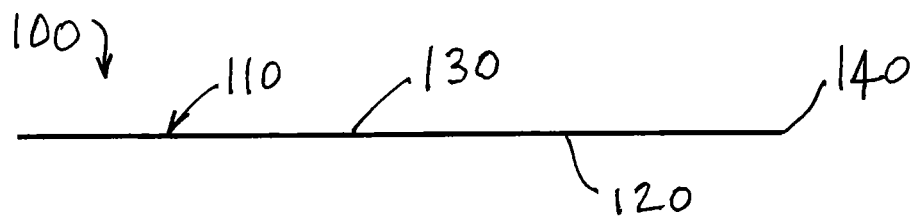
FIG. 5 is a cross-sectional view of the disinfecting cover taken along line 5-5 in FIG. 3.

With reference to FIGS. 3-5, in one embodiment, disinfecting media or cover 100 may be a single thin barrier membrane 110 having a first main surface 120, an opposite second main surface 130, and a peripherally-extending and surrounding edge 140 disposed between the main surface 120 and the opposite second main surface 130. In some embodiments, thin barrier membrane 110 may be a single thin barrier membrane.

With reference again to FIG. 1, the first main surface 120 (FIG. 4) and the opposite second main surface 130 of single thin barrier membrane 110 may be operably sized and configured so that first main surface 120 (FIG. 4) is drapable on top of weight bearing upper surface (FIG. 2) of resilient medical patient pressure redistribution support 10 with peripherally-extending edge 140 terminating between the peripherally-extending side 40 of resilient medical patient pressure redistribution support 10 between weight bearing upper surface 20 (FIG. 2) and bottom surface 30 of resilient medical patient pressure redistribution support 10.

In one embodiment, disinfecting media or cover 100 is installed on the resilient medical patient pressure redistribution support so that peripheral edge portions of the disinfecting media or cover extends below the essentially right-angle transition point or edge defined between the upper planar rectangular surface of the resilient medical patient pressure redistribution support and the vertical sides or boarders.

It will be appreciated that disinfecting media or covers in accordance with aspects of the present disclosure may cover the entire weight bearing upper surface or less than the entire weight bearing upper surface of the resilient medical patient pressure redistribution support. For example, disinfecting media or covers may be sized to extend over a central portion of the upper surface of the resilient medical patient pressure redistribution support, e.g., the peripheral edge of the disinfecting media or cover disposed entirely away from the peripherally-extending sides of the resilient medical patient pressure redistribution support. In other aspects, disinfecting media or covers may be sized to extend over a central portion of the upper surface of the resilient medical patient pressure redistribution support, e.g., the peripheral edge of the disinfecting media or cover extending from one vertical edge to an opposite vertical edge and spaced from the other opposite vertical edges. Other sized and configured disinfecting media or covers that extend over the upper surface and only portions of the resilient medical patient pressure redistribution support may be suitably employed.

It will also be appreciated that disinfecting media or covers in accordance with aspects of the present disclosure may cover the entire upper vertical side portion surrounding the weight bearing upper surface of the resilient medical patient pressure redistribution support, or less than the entire upper vertical side portion surrounding the weight bearing upper surface of the resilient medical patient pressure redistribution support. For example, disinfecting media or covers may cover an entire weight bearing upper surface and extend over only the longer vertical side edges, e.g., not extend over the shorter vertical side or footer and head boarders. Other sized and configured disinfecting media or covers that extend over the vertical side portions of the resilient medical patient pressure redistribution support may be suitably employed.

In some embodiment, disinfecting media or covers may extend over about 50-percent of the resilient medical patient pressure redistribution support. For example, disinfecting media or covers may extend over the entire weight bearing upper surface and half of the vertical sides. In some embodiment, disinfecting media or covers may extend over about 40-percent of the resilient medical patient pressure redistribution support. For example, disinfecting media or covers may extend over only the entire weight bearing upper surface, or only a portion of the weight bearing upper surface and a portion of the vertical sides. In some embodiments, disinfecting media or covers may extend over between about 50-percent and 60-percent of the resilient medical patient pressure redistribution support. In still other embodiments, disinfecting media or covers may extend over less than about 50-percent of the resilient medical patient pressure redistribution support.

As described in greater detail below, the thin barrier membrane may comprise an anti-microbial disinfectant, the thin barrier membrane may be non-fibrous and impervious to the transfer of fluid from the first main surface to the second main surface, and the thin barrier membrane may comprise a thickness operable to maintain the weight distribution of a patient on the weight-bearing surface of a resilient medical patient pressure redistribution support substantially the same compared to the weight distribution of the patient on the weight-bearing surface of a resilient medical patient pressure redistribution support without the single thin barrier membrane.

Figure 6:
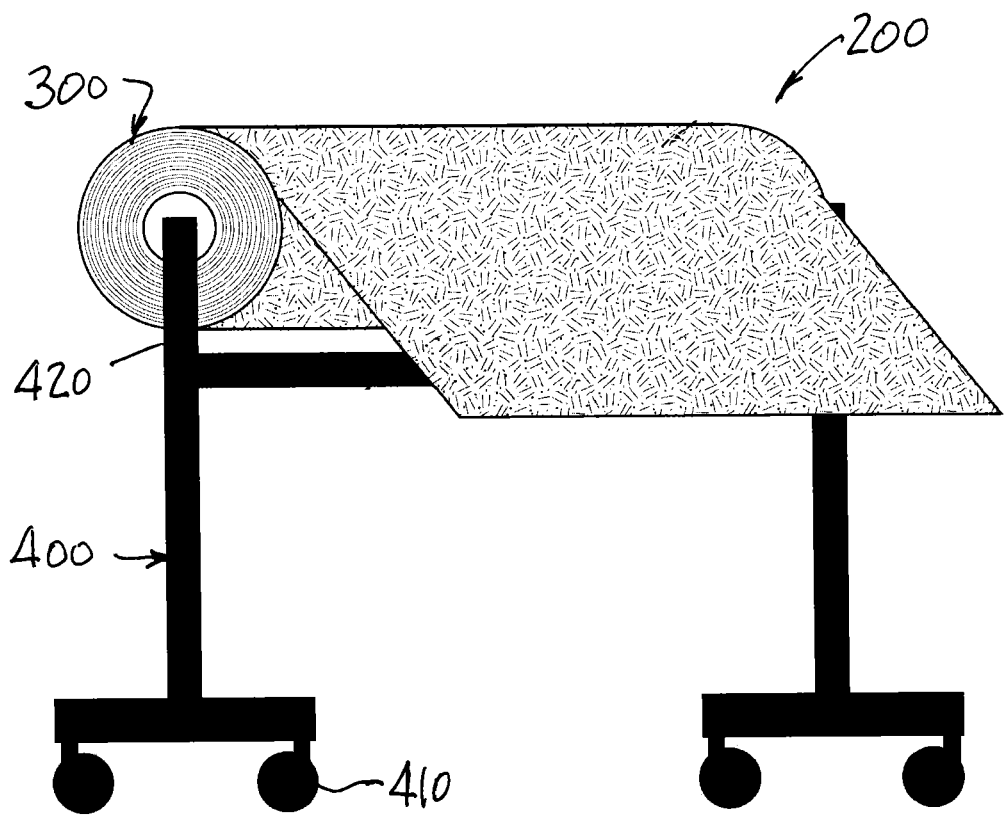
FIG. 6 is an isometric view of one embodiment of a dispensing apparatus in accordance with aspects of the present disclosure for use in disinfecting a plurality of resilient medical patient pressure redistribution supports.

FIG. 6 illustrates an isometric view of one embodiment of a dispensing apparatus 200 comprising a disinfecting cover roll 300 and a roll support apparatus 400 in accordance with aspects of the present disclosure for use in disinfecting a plurality of resilient medical patient pressure redistribution supports. Roll 300 and roll support apparatus 400 may facilitate installation on a resilient medical patient pressure redistribution support. For example, the roll 300 and roll support apparatus 400 may be moved adjacent to a resilient medical patient pressure redistribution support, e.g., to the foot of a bed, and a length of disinfecting cover may be removed and draped over the weight bearing upper surface and then cut from the roll. The apparatus may be constructed with wheels or casters 410 to promote mobility or portability, and a lateral support member 420 disposed at a height sufficient to allow the apparatus to be moved with the roll positioned above or at a higher location or point relative to the weight bearing upper surface of the resilient medical patient pressure redistribution support. The roll may have nominal static cling properties and formed in a continuous sheet measuring about 100 linear yards, less than 100 linear yards, or more than 100 linear yards.

In some embodiments, installation of the disinfecting cover may be performed prior to the first use of a new resilient medical patient pressure redistribution support. For example, a resilient medical patient pressure redistribution support may be placed on a bed frame, and then dispensing apparatus 200 may be aligned so that the leading edge would be affixed partially down the foot or head of the resilient medical patient pressure redistribution support. Then the apparatus may be rolled above the length of the surface (preferably by only one custodial or maintenance person in a healthcare environment). The distance between the spaced-apart supports 420 of dispensing apparatus 200 being wider than the width, for example, of the bed. The disinfecting cover could be attached to the vertical sides or perimeters for the resilient medical patient pressure redistribution support mechanical attachment methods such as clips or hook and loop style fastening systems. Alternatively the disinfecting cover may have static-cling type adhesive properties that secure the disinfecting cover to the resilient medical patient pressure redistribution support.

Figure 7:
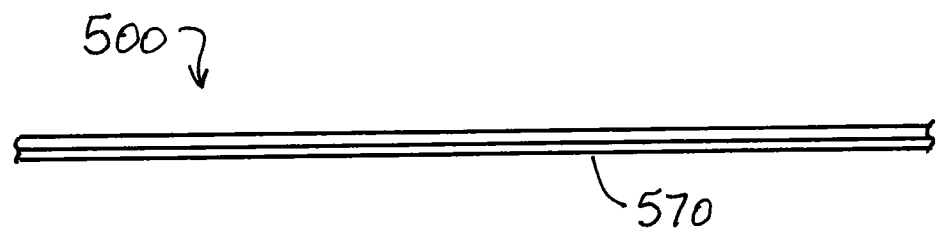
FIG. 7 is a cross-sectional view of another embodiment of a disinfecting cover in accordance with aspects of the present disclosure.
Figure 8:
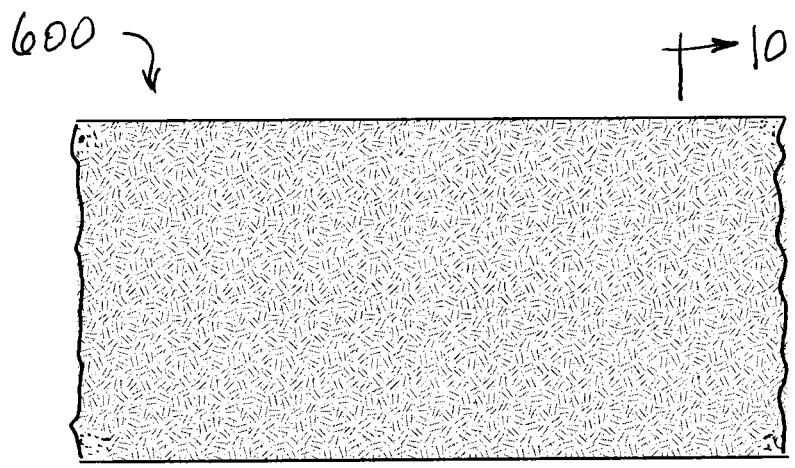
FIGS. 8 and 9 are a top view and a bottom view, respectively, of another embodiment of a disinfecting cover in accordance with aspects of the present disclosure.
Figure 9:
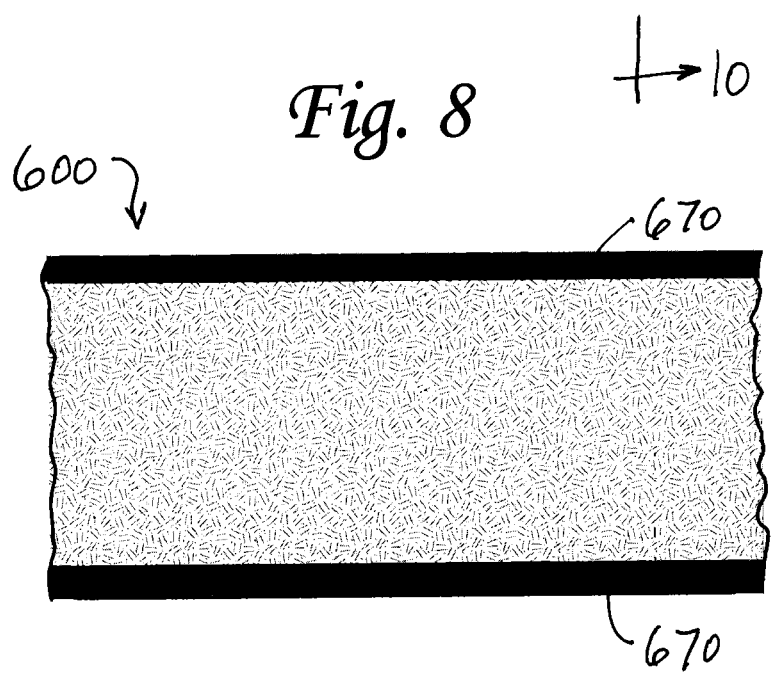
Figure 10:
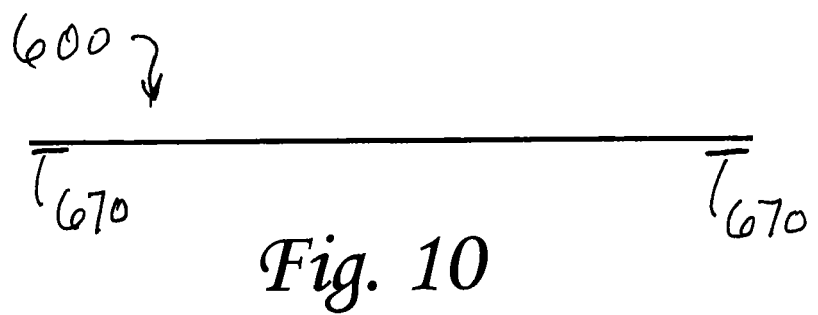
FIG. 10 is a cross-sectional view of the disinfecting cover taken along line 10-10 in FIG. 8.

With reference to FIG. 7, in other embodiments, a disinfecting cover 500 may include an adhesive 570. The adhesive properties may be imparted to the cover during the fabrication process. For example, disinfecting media or cover 500 may include use of a non-permanent adhesive to that the adhesive properties may reduce or limit the propensity of the disinfecting cover shifting while in use under a patient or resting body. Adhesives selected from those with non-permanent and non-frangible properties may be preferred as the break off of adhesive from the cover media that might cause adhesive residue to remain on the support surface following removal of the media may not be desirable. In some embodiments, an adhesive may be disposed along the entire main surface of the cover. In other embodiments, for example, as shown in FIGS. 8-10, a disinfecting cover 600 similar to disinfecting cover 200, may include adhesive 670 disposed along the longitudinal edge portions so that the edges with adhesive may engage the vertical sides of the resilient medical patient pressure redistribution support. In other embodiment, for example, disinfecting cover 100 (FIGS. 3-5) may include adhesive disposed along about 1 inch to 3 inches adjacent to the peripherally-extending edge along the four peripheral edges.

Figure 11:
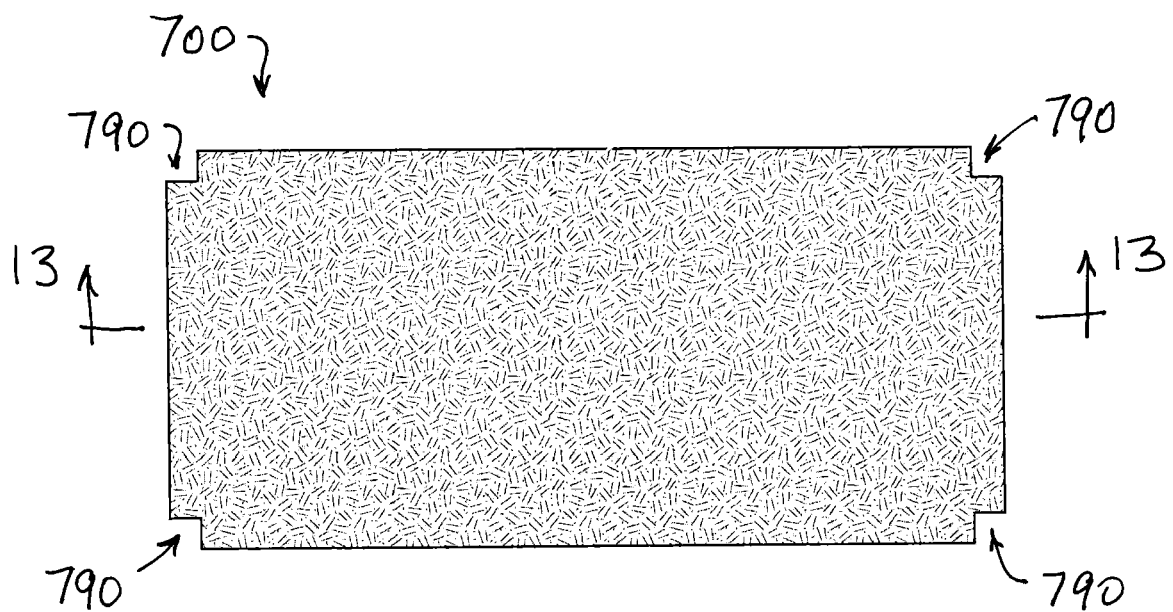
FIG. 11 is a top view of another embodiment of a disinfecting cover in accordance with aspects of the present disclosure.
Figure 12:
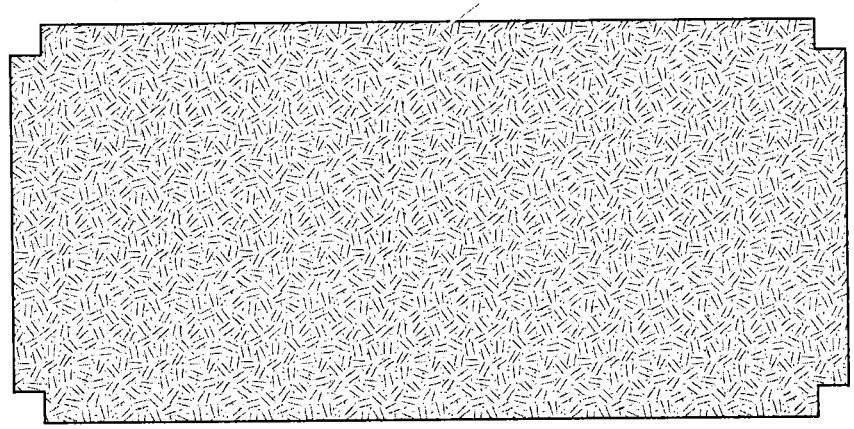
FIG. 12 is a bottom view of the disinfecting cover of FIG. 11.
Figure 13:
FIG. 13 is a cross-sectional view of the disinfecting cover taken along line 13-13 in FIG. 11.

FIGS. 11-13 illustrate a disinfecting cover 700 such as in a die-cut, sheet form. Single sheets of the media could be installed on the surface by cleaning or maintenance staff if so desired. The sizes of specialized healthcare support surface, while subject to some variance are typically similar or fall into several size groupings. Die-cut sheets may be formed for the most common sizes as an alternative to a single roll width. The die-cuts could also be prepared for surface sizes that are not compatible with the roll sizes produced. The corners of the disinfecting cover may include cutouts 790 to allow the peripheral edge to fold over the sides of the resilient medical patient pressure redistribution support without overlapping.

The present disclosure is directed to disinfecting covers and media for use with resilient medical patient pressure redistribution support. Such resilient medical patient pressure redistribution supports may include as mattresses and wheelchair cushions, as well as specialized medical support devices, including, but not limited to pillows, bolsters, positioners, and support wedges. Specialized medical support devices are further listed in the 21 CFR, Parts 862 through 892. The FDA has a list of medical devices that it maintains on its website—some of the classification supported by the CFR sections listed in the following excerpt, "Most medical devices can be classified by finding the matching description of the device in Title 21 of the Code of Federal Regulations (CFR), Parts 862-892. FDA has classified and described over 1,700 distinct types of devices and organized them in the CFR into 16 medical specialty "panels" such as Cardiovascular devices or Ear, Nose, and Throat devices. These panels are found in Parts 862 through 892 in the CFR. For each of the devices classified by the FDA the CFR gives a general description including the intended use, the class to which the device belongs (i.e., Class I, II, or III), and information about marketing requirements. Your device should meet the definition in a classification regulation contained in 21 CFR 862-892."

In some embodiments, the disinfecting media or covers of the present disclosure may be formed individually from or in combinations from the following materials such as polyurethane, poly-vinyl chloride, polyethylene, polypropylene, natural rubber, synthetic rubber, latex, acrylic, polyester, polyvinylidene chloride (PVdC), polythene, or polypropylene carbonate (PPC). The preceding list is not intended to be limiting and compositions that exhibit physical properties similar to the foregoing identified materials but not listed herein may be suitable and are therefore contemplated by the present disclosure.

The disinfecting media or cover may be a film comprising the materials described above and manufactured with antimicrobial materials or antibacterial materials. For example, the material may include, but not limited to, quaternary ammonium, triclosan, metal ions or metal salts, chitosan, cyclodextrin. Other antimicrobials may include ULTRA-FRESH® and SILPURE® antimicrobial products available from Thomson Research Associates of Toronto, Canada. AEGIS MICROBE SHIELD®, available from Microban International, which includes silanes, an active ingredient that forms a colorless, odorless, positively charged polymer that molecularly bonds to the treated surface. Silanes are extremely efficient bonding agents that can be coupled to other molecules and then used to permanently bond those molecules to a target surface. When a microorganism comes in contact with the treated surface, the C-18 molecular punctures the cell membrane and the electrical charge shocks the cell. Since nothing is transferred to the now dead cell, the antimicrobial doesn't lose strength and the molecule is ready for the next cell to contact it. VINYZENE™, available from Dow Chemical, an antimicrobial solution of 4,5-dichloro-2-n-octyl-4-isothiazolin-3-one in a nonvolatile plasticizer carrier, effective for use in vinyl, polyurethane and other polymeric compositions. Low levels of VINYZENE™ antimicrobials will provide long term preservation against a broad spectrum of bacterial and fungal organisms and will help inhibit surface growth, permanent staining, embrittlement and premature product failure. The various materials may be incorporated into the polymer or film during normal processing steps. The disinfecting antimicrobial material may be disposed generally throughout the cover, or reside adjacent to one or both main surfaces. Alternatively, the disinfecting cover or media may be a laminate comprising a plurality of different layers. For example, a film having one or more outer antimicrobial material coatings.

The thickness of the disinfecting media or cover may be about 0.5 mils, or about 12.5 µm. In other embodiments, the thickness of the disinfecting media or cover may range from about 0.1 mils to about 3.0 mils, about 0.1 mils to about 0.5 mils, from about 0.5 mils to about 1.0 mil, from about 1.0 mil to about 2.0 mils, and about 2.0 mils to about 3.0 mils. The thickness of the disinfecting media or cover may also be about 0.1 mil, about 0.5 mils, about 1.0 mil, about 2.0 mils, or about 3.0 mils. It will be appreciated that other thickness may be suitably employed. The disinfecting media or cover may be uniform or non-uniform in thickness.

In connection with the various embodiments, the term of use intended for the disinfecting covers or media of the present disclosure may be limited to the duration of a single patient's use of the surface or an even shorter period if the cleaning and maintenance guidelines for the healthcare facility so dictate. The removal of the media from the support surface could be done by custodial, maintenance or even care-providing staff. It is anticipated that formation of the disinfecting cover or media may be done from materials that could be sanitized and subsequently recycled for use again in the same application. The material selection is also contemplated wherein materials could permit simultaneous sanitization and recycling.

In its typical use cycle, a weight support surface with the media 100 (FIG. 1) installed may be used by a patient. When it was determined that surface was ready to be cleaned, the bedding 50 (FIG. 1) (sheets, pillow, mattress pads, draw sheets, etc.) would be removed and customary laundering would be performed on these articles. Then the installed disinfecting cover or media 100 (FIG. 1) may be visually inspected for signs of breach, damage or fluid strike-through. The media 100 (FIG. 1) would then be removed and discarded pursuant to the disposal protocols of the medical facility. The support surface would itself be visually examined for evidence of fluid strike through. If the visual examination indicated no strike-through to the textile surface of the medical support surface then low-level cleaning could be performed—for instance, wiping down with sanitized solutions and drying. If the visual examination did reveal strike-through potential, then more aggressive cleaning measures could be applied to the medical support surface. It is the intention that the disinfecting cover or media and its protective nature may permit less frequent and less aggressive cleaning approaches to be taken on specialized medical support surfaces. By their nature the cleaning approaches needed in healthcare environments are destructive and damaging to the surfaces being cleaned as they need to attempt to kill the pathogens that are identified as posing risks to patients and causing HAI's, and therefore can reduced the expected service lives of the articles being cleaned.

Figure 14:
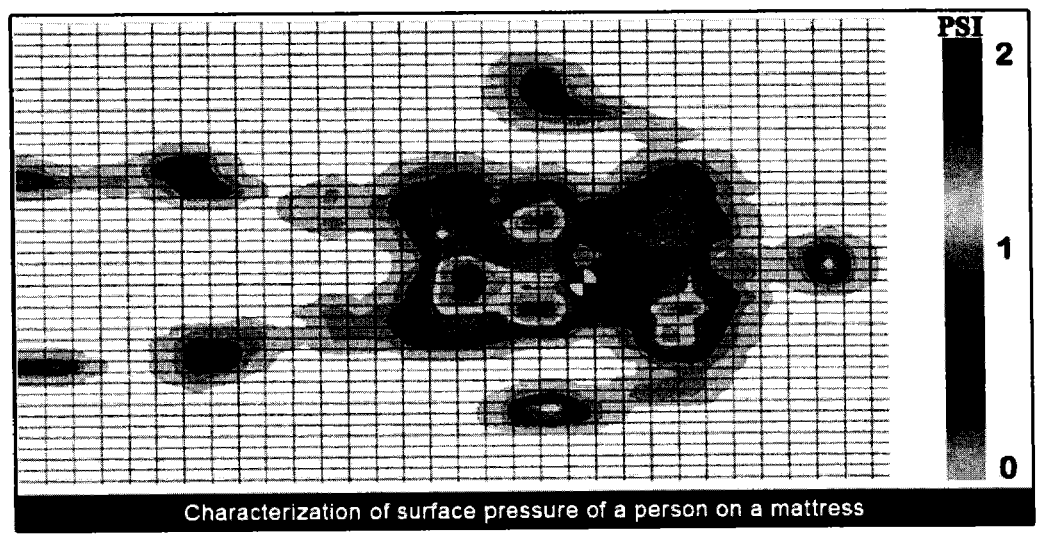
FIG. 14 is an illustration of a pressure mapping reading taken from a resilient medical patient pressure redistribution support.

In some embodiments, a minimal differential in force per unit area exerted perpendicularly to the planar surface of the medical patient support surface device may be seen with or without the disinfecting cover or media installed on the surface. For example, FIG. 14 illustrates a pressure mapping reading taken from a support surface. In healthcare settings, the need to protect patients from skin breakdown and decubitus ulcer (bedsore) formation may be a desired clinical objective. The design and manufacture of specialized medical support surfaces places a high level of importance on the pressure-relieving characteristics of such surfaces. A visual representation of these design elements as provided by a pressure map can be a helpful tool to care providers.

In aspect of the present disclosure, disinfecting covers or media and methods for disinfecting a specialized, medical patient support surface device is designed for pressure redistribution is provided. In some embodiments, a method may include installing a substantially uniform, non-liquid and non-fibrous polymer based media so as to cover at least one planar surface of said device and allows for immediate, post-installation patient use, while simultaneously providing resistance to blood-borne pathogen and viral penetration and greater than 99% contact inhibition to at least one of the following:

Methicillin resistant *Staphylococcus aureus* (MRSA);
*Aspergillus niger;*
*Staphylococcus aureus;*
*Clostridium difficile* (*C. Diff*); and
*Escherichia coli* (*E. coli*);

and may also not increase the force per unit area exerted perpendicularly to the planar surface of the medical patient surface device.

FIG. 15 illustrates a method 800 for disinfecting a weight bearing upper surface of a resilient medical patient pressure redistribution support in which the resilient medical patient pressure redistribution support includes a lower surface, and a peripherally-extending side disposed between the weight bearing upper surface and the lower surface. The method includes at 810, providing a disinfecting cover having a first main surface, an opposite second main surface, and a peripherally-extending edge, the disinfecting cover being non-fibrous and comprising an anti-microbial disinfectant, and at 820, draping the first main surface of the disinfecting cover over the weight bearing upper surface of the resilient medical patient pressure redistribution support with portions of the first main surface, the opposite second main surface, and the peripherally-extending edge of the disinfecting cover extending away from the weight bearing upper surface. At 830, portions of the first main surface, the opposite second main surface, and the peripherally-extending edge extending away from the weight bearing upper surface is positioned below the weight bearing upper surface of the resilient medical patient pressure redistribution support and over a portion of the peripherally-extending side of the resilient medical patient pressure redistribution support with the peripherally-extending edge of the planar disinfecting cover disposed above the lower surface of resilient medical patient pressure redistribution support. At 840, the disinfecting cover is releasably secured in position over the weight bearing upper surface and along the peripherally-extending side of the resilient medical patient pressure redistribution support. The disinfecting cover may comprises a thickness operable to maintain the weight distribution of a patient on the weight bearing upper surface of the resilient medical patient pressure redistribution support substantially the same compared to the weight distribution of the patient on the weight bearing upper surface of the resilient medical patient pressure redistribution support without the disinfecting cover.

In some embodiments, the disinfecting cover may be about 37 inches to about 42 inches wide, and about 82 to about 87 inches long, for example for use on a bed mattress having dimensions of about 35 inches wide by about 80 inches long by about 6 inches deep. In other embodiments, the disinfecting cover may be about 22 inches or about 26 inches wide to about 22 inches or about 26 inches long, for example for use on a seat having dimensions of about 18 inches to about 22 inches wide by about 18 inches to about 22 long by about 4 inches deep. The peripheral edge portion may extend about 1 inch to about 3 inches over the sides of the supports, and desirably about 2 inches over the sides of the supports. In other embodiment, the disinfecting comer may be disposable.

Exemplary Embodiment

Development of a disinfecting cover or media may be described as follows. A standard, specialized medical patient support surface may be selected, for example, the size of the selected support surface may measures 35 inches wide by 80 inches long by 6 inches deep.

The disinfecting cover or media may be selected from a polyurethane based film that is manufactured with anti-microbial chemistries and nominal static cling properties is formed in a continuous sheet measuring about 100 linear yards. Alternative compositions for the media may be selected individually or from combinations of the following: polyurethane, poly-vinyl chloride, polyethylene, polypropylene, natural rubber, synthetic rubber, latex, acrylic, polyester, polyvinylidene chloride (PVdC), polythene, or polypropylene carbonate (PPC). The preceding list is not intended to be limiting and compositions that exhibit physical properties similar to the foregoing identified materials but not listed herein may be suitable and are therefore contemplated by the present disclosure.

The roll of film described herein may be installed on a dispensing apparatus that facilitates the placement of film from the head or foot end of the specialized medical patient support surface.

After removal of bed clothes 50 (FIG. 1) and previously installed protective media 100, the surface 20 (FIG. 2) is inspected and optionally cleaned to the degree deemed appropriate by the custodial, maintenance, or care-giving staff, then the media installation commences from one end of the surface and the dispensing apparatus is moved to a position at the opposite end of the surface thereby dispensing the media 100 (FIG. 1) across the length of the upper planar face of the support surface. The media is smoothed across the specialized medical support surface and cut off from the roll when sufficient quantity of material has been dispensed. Excess media is smoothed down the sides at all four sides of the support surface and then the bedding 50 (e.g. mattress pads, sheets, draw sheets, pillows and blankets) are reinstalled on the surface, thereby making it ready for use by the next patient.

The installed media is intended to deliver in-place disinfection to the surfaces of the specialized medical support surface to which the disinfecting cover or media is in contact during its period of installation. The following table lists certain organisms that preferred embodiments of the present disclosure may be operable or engineered to kill or reduce while in use and selected test methods customarily used to assess the efficacy of performance against such organisms.

TABLE 1

| Organism Type | Organism | Test Method | Organism Load | Result Required* |
|---|---|---|---|---|
| Bacteria | Methicillin Resistant Staphylococcus aureus (MRSA) | ISO 22196:2007 | ATCC #33591 | Contact Inhibition >99% or % Survival <0.1% |
| | | or | | |
| Bacteria | Methicillin Resistant Staphylococcus aureus (MRSA) | AATCC Method 147-2004 | ATCC #33591 | Contact Inhibition >99% or % Survival <0.1% |
| Fungus | Aspergillus niger | AATCC Method 30-1988 | ATCC #6275 | Contact Inhibition >99% or % Survival <0.1% |
| Bacteria | Staphylococcus aureus | AATCC Method 147-1988 | Not provided | Contact Inhibition >99% or % Survival <0.1% |
| Bacteria | Clostridium difficile (C. Diff) | AATCC Method 147-1988 | Not provided | Contact Inhibition >99% or % Survival <0.1% |
| Bacteria | Escherichia coli | AATCC Method 147-2004 | ATCC #8739 | Contact Inhibition >99% or % Survival <0.1% |

*Result reporting approach is determined by test method used.

Additionally, the cytotoxicity and skin irritation profile of the cover or media may require evaluation in certain circumstances as part of the determination for their fitness for use and therefore evaluated to demonstrate that it may not have potentially adverse consequences for patients in the event of direct skin to media contact in the use environment. Customary evaluations for this parameter include:
  ISO 10993-5: Biological Examination of Medical Devices Part 5: Tests for Cytotoxicity, In Vitro Methods, or
  ISO 10993-10: Biological Examination of Medical Devices Part 10: Tests for Irritation and Sensitization.

The test methods identified herein for assessment of the performance attributes of substantially uniform, non-liquid and non-fibrous polymer based cover or media of the present disclosure relative to anti-microbial protection, moisture vapor transmission and blood-borne and viral transmission are intended to be exemplary and not limiting to the scope of this disclosure. All cited test methods are hereby incorporated in their entirety by reference.

In 2007, the Centers for Disease Control (CDC) reported data for 2002, which estimated the number of HAIs in U.S. hospitals, adjusted to include federal facilities, was approximately 1.7 million: 33,269 HAIs among newborns in high-risk nurseries, 19,059 among newborns in well-baby nurseries, 417,946 among adults and children in ICUs, and 1,266,851 among adults and children outside of ICUs. The estimated deaths associated with HAIs in U.S. hospitals were 98,987: of these, 35,967 were for pneumonia, 30,665 for bloodstream infections, 13,088 for urinary tract infections, 8,205 for surgical site infections, and 11,062 for infections of other sites.

In guiding healthcare professionals regarding disinfection practices for specialized medical patient support surfaces, the CDC has offered the following: "Standard mattresses and pillows can become contaminated with body substances during patient care if the integrity of the covers of these items is compromised. The practice of sticking needles into the mattress should be avoided. A mattress cover is generally a fitted, protective material, the purpose of which is to prevent the mattress from becoming contaminated with body fluids and substances. A linen sheet placed on the mattress is not considered a mattress cover. Patches for tears and holes in mattress covers do not provide an impermeable surface over the mattress. Mattress covers should be replaced when torn; the mattress should be replaced if it is visibly stained. Wet mattresses, in particular, can be a substantial environmental source of microorganisms. Infections and colonizations caused by *Acinetobacter* spp., MRSA, and *Pseudomonas aeruginosa* have been described, especially among burn patients. In these reports, the removal of wet mattresses was an effective infection-control measure. Efforts were made to ensure that pads and covers were cleaned and disinfected between patients using disinfectant products compatible with mattress-cover materials to ensure that these covers remained impermeable to fluids. Pillows and their covers should be easily cleanable, preferably in a hot water laundry cycle. These should be laundered between patients or if contaminated with body substances.

Specialized patient support surfaces or hospital mattresses have been identified as a leading contact point for patients during stays in healthcare facilities. There is evidence that cleaning and disinfecting procedures for such surfaces are frequently ineffective and that when effectively practiced can result in damage and shortened service life for the surfaces. Additionally, the labor (man-hour) intensity, natural resource consumption (water) and chemical usage are factors that place burdens on healthcare facilities to successfully deploy effective cleaning and disinfection protocols.

In addition to the labor burdens and material costs associated with effective, and often aggressive, cleaning and disinfection protocols, excess water usage and use of toxic cleaning agents, many of which may be chlorine-based, may have deleterious and therefore undesirable environmental consequences.

The traditional design approach for specialized patient support surfaces has been to use a resilient filling material, such as polyurethane foam, to build a mattress core. A fluid-proof outer cover has then been installed over the core.

Designs of fluid-proof outer covers historically incorporated poly-vinyl chloride (PVC) based coatings. PVC was once desirable for use as it permitted very low levels of moisture vapor transmission rates (MVTR—as measured transmission of water vapor through the cover on a grams per meter$^2$ basis by test protocol ASTM E96/BW) through the outer fabric cover. The MVTR was seen as indicative of or a proxy for the amount of potential pathogen laden vapor that could migrate from the patient to the inner core of the surface; therefore cover materials with no or very low measured levels of moisture vapor transmission were deemed desirable. Unfortunately, PVC coatings exhibited a propensity to crack during their service life. This cracking, typically caused by plasticizer migration, resulted in breaches to the fluid-proof properties and a resultant potential for "strike-through" of fluids and other contaminants and pathogens to the interior core structure. Therefore in ordinary use, the PVC might preclude transmissive pathogen passage to the interior of the surface, but once cracking occurred the inherent protection was immediately and irreversibly compromised.

Improved design approaches for specialized patient support surfaces have, in many cases, replaced PVC content with polyurethane based coatings and films or rubber based coatings and films. In many healthcare settings, medical professionals tasked with managing the infection control protocols for their facilities can exercise significant control over the decision making for material purchases for their facilities. In the case of specialized patient support surfaces, these individuals have, for instance, identified certain fabrics with rubber based coatings as preferred for use since the rubber materials imparts rates of moisture vapor transmission comparable to those seen in PVC materials. A customary measure of moisture vapor transmission through a textile or medical use fabric is ASTM E96/BW that is incorporated in its entirety herein by reference.

An additionally desirable attribute related to high performance medical fabrics is the ability of the material to withstand penetration of blood, bodily fluids, viral materials or blood- or bodily fluid-borne pathogens. The ability of the textile material to perform as desired in this regard is customarily evaluated through testing to protocols such as ASTM F1670, ASTM F1671, ISO 16603:2004 or ISO 16604:2004 and the provisions and requirements of the these tests are also incorporated in their entirety herein by reference.

The emergence of requirements that mattresses in high-risk occupancies such as hospitals meet full-scale, open flame resistant testing such as California Technical Bulletin #129, 16 CFR 1633 or Boston Fire Department IX-11 has added the placement of fire barrier materials that are disposed between the core and cover, as well as the use of chemical flame retardant additives to the core materials and cover fabrics.

Industry's recognition of the limitations on facility based cleaning and disinfecting has in large part contributed to the increased use of and reliance on anti-microbial and anti-fungal agents and compounds in the production of the outermost fabrics or tickings used in the construction of specialized patient support surfaces. The efficacy of such anti-microbial treatments is customarily demonstrated by results of kill rates or zones of inhibition measured by test protocols such as ISO 22196, AATCC Method 147, or AATCC Method 30. These test protocols are incorporated herein in their entirety by reference. Alternative test protocols not identified herein that seek to assess the efficacy of such treatments are contemplated and their use would not be considered a departure from the present disclosure.

Not only have anti-microbial agents been integrated into healthcare fabrics using traditional methodologies where a chemical compound or liquid is added to the coating medium (e.g. polyurethane or rubber), there has been an increasing use of nano-particle-based anti-microbial technologies. There is meaningful debate still occurring regarding not only the efficacy but the safety of these approaches, which are alternatively referred to or marketed as "metal ion" based or "soluble glass carrier" based. Concerns have been voiced that the introduction of metal ion based nanoparticle based anti-microbial technologies have a potentially adverse effect on aquatic life populations as the nanomaterials may wash off of textiles treated with these materials during laundering and enter aquatic eco-systems where their persistent biocidal capacities continue unabated.

Some approaches to deal with controlling microbial pathogens on specialized medical patient support surfaces have sought to add an additional, removable and launderable cover to the outside of the support surface. These are complex and labor intensive to install. They are expensive to manufacture and the reusable, launderable nature of such covers requires resource consumption in terms of water and energy, not to mention usage of detergents. Furthermore, when these expensive solutions suffer mechanical penetration or breaching of their own outermost fabric layers, they too are no longer capable of fully performing as originally intended.

Regardless of the specific approach to anti-microbial used in the outer fabrics of specialized patient support surfaces, there are critical issues related to long-term durability and speed of effect that have meaningful bearing on the ability for these to work effectively as intended. Certain agents (and this is substantiated by testing that reveals a "zone of inhibition" or "halo-effect" for its kill radius) perform be leaching away from the point of initial treatment.

In addition to the surface growth of microbial organisms and pathogens, healthcare providers and occupancies must be alert for breaches in the outermost fabric covers caused by physical/mechanical damage resulting from the actions of medical professionals and patients. The stabbing of hypodermic needles ("sharps") into mattresses can in the course of care of patients breach the outer cover. Other avenues for damage to the intended fluid-impermeable design of the support surface can include, but are by no means limited to, the dragging of equipment across the surface cover fabric, dragging or sliding of patients across the uppermost, planar surface of the article, vigorous and abrasive cleaning techniques, the use of damaging cleaning agents and failure to fully remove residual chemistries post-cleaning, and improperly using cleaning agents not intended for textiles and others materials used to manufacture specialized medical patient support surfaces.

The clinical requirements for specialized medical patient support devices necessitate that manufacturers of such devices select textiles and filling materials so as to permit the design and construction of such devices in a manner that will support the medical clinicians need to satisfactorily address the challenges of impaired skin integrity and do so by redistributing or reducing interface pressures of the patient body areas in contact with the support surface.

Customarily the design of specialized medical patient support devices is evaluated with regards to interface pressures using the visual representations of pressure mapping.

A pressure map is a computerized clinical tool for assessing pressure distribution. To use it, you place a thin, sensor mat on a wheelchair seat or a mattress surface. A patient sits or lies on the mat, a computer screen displays a map of pressures, using colors, numbers, and a graphic image of the patient. Typically, the hotter colors (the reds) indicate areas of higher pressures, and the cooler colors (the blues) indicate areas of lower pressures. The display usually has several options, including a three-dimensional display of peak pressure areas and a statistical analysis.

Pressure mapping does have some drawbacks, including inconsistencies in the ways manufacturers report and display the pressures, differences in measurable peak pressures among manufacturers, and sensor accuracy and drift. Still, these visual displays provide key data that can augment nursing assessment of the areas of potential tissue damage and therefore take prophylactic measures in the direction of preventing decubitus ulcer formation.

There is a key nexus between infection control and interface pressure control. The formation of decubitus ulcers or "bed sores" is more likely to strike patients facing profound ambulatory and mobility challenges. These patients at are therefore more susceptible to and at higher risk of contracting HAI's. The measures needed to control infections must therefore be not only efficacious in terms of controlling and eradicating microbial and pathogen growth in the medical environment; the measures must also not cause a measureable or significant alteration to the control of patient interface originally engineered into specialized medical patient support surfaces.

It is to be understood that the above description is intended to be illustrative, and not restrictive. For example, the above-described embodiments and/or aspects thereof may be used in combination with each other. In addition, many modifications may be made to adapt a particular situation or material to the teachings of the various embodiments without departing from their scope.

While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

It is to be understood that not necessarily all such objects or advantages described above may be achieved in accordance with any particular embodiment. Thus, for example, those skilled in the art will recognize that the systems and techniques described herein may be embodied or carried out in a manner that achieves or optimizes one advantage or group of advantages as taught herein without necessarily achieving other objects or advantages as may be taught or suggested herein.

While the disclosure has been described in detail in connection with only a limited number of embodiments, it should be readily understood that the disclosure is not limited to such disclosed embodiments. Rather, the disclosure can be modified to incorporate any number of variations, alterations, substitutions, or equivalent arrangements not heretofore described, but which are commensurate with the spirit and scope of the disclosure. Additionally, while various embodiments of the disclosure have been described, it is to be understood that aspects of the disclosure may include only some of the described embodiments. Accordingly, the disclosure is not to be seen as limited by the foregoing description, but is only limited by the scope of the appended claims.

This written description uses examples, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A method for disinfecting a weight bearing upper textile surface of a resilient medical patient pressure redistribution support, the resilient medical patient pressure redistribution support further comprising a lower surface, and a peripherally-extending side disposed between the weight bearing upper surface and the lower surface, the method consisting of:
   removing a support covering from the resilient medical patient pressure redistribution support to expose the weight bearing upper textile surface of the resilient medical patient pressure redistribution support;
   providing a disinfecting single uniform barrier polymer membrane having static cling properties, a first main surface, an opposite second main surface, and a peripherally-extending edge, the disinfecting membrane being non-fibrous, impervious to the transfer of liquid from the first main surface to the second main surface, and comprising an anti-microbial disinfectant, the disinfecting single uniform barrier polymer membrane sized to not cover the lower surface of the resilient medical patient pressure redistribution support;
   draping the first main surface of the disinfecting single uniform barrier polymer membrane directly on the weight bearing upper textile surface of the resilient medical patient pressure redistribution support with portions of the first main surface, the opposite second main surface, and the peripherally-extending edge of the disinfecting membrane extending away from the weight bearing upper textile surface;
   positioning the portions of the first main surface, the opposite second main surface, and the peripherally-extending edge extending away from the weight bearing upper textile surface below the weight bearing upper surface of the resilient medical patient pressure redistribution support and over a portion of the peripherally-extending side of the resilient medical patient pressure redistribution support;
   releasably securing the disinfecting single uniform barrier polymer membrane with static electricity in position over the weight bearing upper textile surface and along the peripherally-extending side of the resilient medical patient pressure redistribution support so that the disinfecting single uniform barrier polymer membrane does not extend over the lower surface of the resilient medical patient pressure redistribution support;
   disposing a support covering over and onto the second main surface of the releasably secured disinfecting single uniform barrier polymer membrane on the resilient medical patient pressure redistribution support;
   wherein the disinfecting single uniform barrier polymer membrane having the anti-microbial disinfectant is efficacious in the killing of pathogens associated with causing healthcare-associated infections;
   wherein the disinfecting membrane comprises a thickness operable to maintain the weight distribution of a patient on the weight bearing upper textile surface of the resilient medical patient pressure redistribution support substantially the same compared to the weight distribution of the patient on the weight bearing upper textile surface of the resilient medical patient pressure redistribution support without the disinfecting membrane; and
   wherein the disinfecting single uniform barrier polymer membrane having the anti-microbial disinfectant is operable for greater than 99% of contact inhibition.

2. The method of claim 1 wherein the providing the disinfecting membrane comprises providing the disinfecting membrane sized to extend over only between 40 percent and 60 percent of the resilient medical patient pressure redistribution support.

3. The method of claim 1 wherein the providing the disinfecting membrane comprises providing the disinfecting membrane sized to extend over only 50 percent of the resilient medical patient pressure redistribution support.

4. The method of claim 1 wherein the draping comprises draping the first main surface of the disinfecting membrane over the weight bearing upper textile surface of the resilient medical patient pressure redistribution support without moving the resilient medical patient pressure redistribution support.

5. The method of claim 1 wherein the draping comprises draping the first main surface of the disinfecting membrane over the entire weight bearing upper textile surface of the resilient medical patient pressure redistribution support.

6. The method of claim 1 wherein the providing the disinfecting membrane comprises providing the disinfecting membrane having a rectangular configuration.

7. The method of claim 1 wherein the providing the disinfecting membrane comprises providing the disinfecting membrane having a generally rectangular configuration with cutouts disposed at the corners.

8. The method of claim 1 wherein the providing the disinfecting membrane further comprises providing the disinfecting membrane disposed on a roll, and removing the disinfecting membrane from the roll.

9. The method of claim 1 wherein the providing the disinfecting membrane comprises providing a roll of the disinfecting membrane, and cutting the disinfecting membrane from the roll.

10. The method of claim 1 wherein the providing the disinfecting membrane comprises providing a dispensing apparatus comprising a roll of the disinfecting membrane and movable supports, and the draping the disinfecting membrane comprises passing the roll over and the movable supports around the resilient medical patient pressure redistribution support.

11. The method of claim 1 wherein the draping the support covering over the releasably secured disinfecting membrane comprises draping one or more fabric layers over the releasably secured disinfecting cover.

12. The method of claim 11 wherein the draping the one or more fabric layers over the releasably secured disinfecting cover comprises draping bedding over the releasably secured disinfecting membrane.

13. The method of claim 11 wherein the draping the one or more fabric layers over the releasably secured disinfecting membrane comprises draping at least one of mattress pads, sheets, draw sheets, pillows and blankets over the releasably secured disinfecting membrane.

14. The method of claim 1 wherein the disinfecting membrane comprises at least one of the following: polyurethane, poly-vinyl chloride, polyethylene, polypropylene, natural rubber, synthetic rubber, latex, acrylic, polyester, polyvinylidene chloride, polythene, polypropylene carbonate, or combinations thereof.

15. The method of claim 1 wherein the disinfecting membrane comprises a moisture vapor transmission rate of less than 500 grams per meter$^2$ per 24 hour period.

16. The method of claim 1 wherein the anti-microbial disinfectant comprises at least one of quaternary ammonium, triclosan, metal ions, metal salts, chitosan, cyclodextrin.

17. The method of claim 1 wherein the resilient medical patient pressure redistribution support comprises a mattress.

18. The method of claim 1 wherein the resilient medical patient pressure redistribution support comprises a wheelchair cushion.

19. The method of claim 1 wherein the resilient medical patient pressure redistribution support comprises a stretcher or gurney pad.

20. The method of claim 1 wherein the resilient medical patient pressure redistribution support comprise an operating room pad.

21. The method of claim 1 wherein the-disinfecting membrane comprises a generally rectangular configuration with cutouts disposed at the corners so that said disinfecting cover is positionable over the weight bearing upper textile surface of the resilient medical patient pressure redistribution support with the cutouts permitting edges of membrane to extend over the peripheral side edge surfaces of the resilient medical patient pressure redistribution support.

22. The method of claim 1 wherein the disinfecting membrane cover comprises a thickness of 0.5 mils (12.5 μm).

23. The method of claim 1 wherein the disinfecting membrane cover comprises a thickness between 0.5 mils (12.5 μm) and 1 mil (25.4 μm).

24. The method of claim 1 wherein the disinfecting membrane cover comprises a thickness between 0.5 mils (12.5 μm) and 3 mil (76.2 μm).

25. The method of claim 1 wherein the anti-microbial disinfectant is disposed throughout the disinfecting membrane.

26. The method of claim 25 wherein the disinfecting membrane comprises a moisture vapor transmission rate of less than 500 grams per meter$^2$ per 24 hour period.

27. The method of claim 1 wherein the disinfecting single uniform barrier polymer membrane having the anti-microbial disinfectant is operable to simultaneously provide resistance to blood-borne pathogen and viral penetration.

28. The method of claim 1 wherein the disinfecting single uniform barrier polymer membrane having the anti-microbial disinfectant is operable to provide resistance to blood-borne pathogen.

29. The method of claim 1 wherein the disinfecting single uniform barrier polymer membrane having the anti-microbial disinfectant is operable to provide resistance to viral penetration.

30. The method of claim 1 wherein the disinfecting single uniform barrier polymer membrane having the anti-microbial disinfectant is operable for contact inhibition.

31. The method of claim 1 wherein the disinfecting single uniform barrier polymer membrane having the anti-microbial disinfectant is operable for greater than 99% of contact inhibition to methicillin resistant *Staphylococcus aureus* (MRSA).

32. The method of claim 1 wherein the disinfecting single uniform barrier polymer membrane having the anti-microbial disinfectant is operable for greater than 99% of contact inhibition to *Aspergillus niger*.

33. The method of claim 1 wherein the disinfecting single uniform barrier polymer membrane having the anti-microbial disinfectant is operable for greater than 99% of contact inhibition to *Staphylococcus aureus*.

34. The method of claim 1 wherein the disinfecting single uniform barrier polymer membrane having the anti-microbial disinfectant is operable for greater than 99% of contact inhibition to *Clostridium difficile* (*C. Diff*).

35. The method of claim 1 wherein the disinfecting single uniform barrier polymer membrane having the anti-microbial disinfectant is operable for greater than 99% of contact inhibition to *Escherichia coli* (*E. coli*).

36. A method for disinfecting a weight bearing upper textile surface of a resilient medical patient pressure redistribution support, the resilient medical patient pressure redistribution support further comprising a lower surface, and a peripherally-extending side disposed between the weight bearing upper surface and the lower surface, the method consisting of:
    removing a support covering from the resilient medical patient pressure redistribution support to expose the weight bearing upper textile surface of the resilient medical patient pressure redistribution support;
    providing a disinfecting single uniform barrier polymer membrane having a first main surface, an opposite second main surface, and a peripherally-extending edge, the disinfecting membrane being non-fibrous, impervious to the transfer of liquid from the first main surface to the second main surface, and comprising an anti-microbial disinfectant, the disinfecting single uniform barrier polymer membrane sized to not cover the lower surface of the resilient medical patient pressure redistribution support, the disinfecting single uniform barrier polymer membrane comprising an adhesive disposed on at least a portion of the first main surface of the disinfecting membrane;
    draping the first main surface of the disinfecting single uniform barrier polymer membrane directly on the weight bearing upper textile surface of the resilient medical patient pressure redistribution support with portions of the first main surface, the opposite second main surface, and the peripherally-extending edge of the disinfecting membrane extending away from the weight bearing upper textile surface;
    positioning the portions of the first main surface, the opposite second main surface, and the peripherally-extending edge extending away from the weight bearing upper textile surface below the weight bearing upper surface of the resilient medical patient pressure redistribution support and over a portion of the peripherally-extending side of the resilient medical patient pressure redistribution support;
    releasably securing the disinfecting single uniform barrier polymer membrane with the adhesive disposed on the at least the portion of the first main surface in position over the weight bearing upper textile surface and along the peripherally-extending side of the resilient medical patient pressure redistribution support so that the disinfecting single uniform barrier polymer membrane does not extend over the lower surface of the resilient medical patient pressure redistribution support;
    disposing a support covering over and onto the second main surface of the releasably secured disinfecting single uniform barrier polymer membrane on the resilient medical patient pressure redistribution support;
    wherein the disinfecting single uniform barrier polymer membrane having the anti-microbial disinfectant is efficacious in the killing of pathogens associated with causing healthcare-associated infections;
    wherein the disinfecting membrane comprises a thickness operable to maintain the weight distribution of a patient on the weight bearing upper textile surface of the resilient medical patient pressure redistribution support substantially the same compared to the weight distribution of the patient on the weight bearing upper textile surface of the resilient medical patient pressure redistribution support without the disinfecting membrane; and wherein the disinfecting single uniform barrier polymer membrane having the anti-microbial disinfectant is operable for greater than 99% of contact inhibition.

37. A method for disinfecting a weight bearing upper textile surface of a resilient medical patient pressure redistribution support, the resilient medical patient pressure redistribution support further comprising a lower surface, and a peripherally-extending side disposed between the weight bearing upper surface and the lower surface, the method consisting of:

removing a first support covering from the resilient medical patient pressure redistribution support to expose the weight bearing upper textile surface of the resilient medical patient pressure redistribution support;

providing a first disinfecting single uniform barrier polymer membrane having static cling properties, a first main surface, an opposite second main surface, and a peripherally-extending edge, the first disinfecting membrane being non-fibrous, impervious to the transfer of liquid from the first main surface to the second main surface, and comprising an anti-microbial disinfectant, the first disinfecting single uniform barrier polymer membrane sized to not cover the lower surface of the resilient medical patient pressure redistribution support;

draping the first main surface of the first disinfecting single uniform barrier polymer membrane directly on the weight bearing upper textile surface of the resilient medical patient pressure redistribution support with portions of the first main surface, the opposite second main surface, and the peripherally-extending edge of the first disinfecting membrane extending away from the weight bearing upper textile surface;

positioning the portions of the first main surface, the opposite second main surface, and the peripherally-extending edge extending away from the weight bearing upper textile surface below the weight bearing upper surface of the resilient medical patient pressure redistribution support and over a portion of the peripherally-extending side of the resilient medical patient pressure redistribution support;

releasably securing the first disinfecting single uniform barrier polymer membrane with static electricity in position over the weight bearing upper textile surface and along the peripherally-extending side of the resilient medical patient pressure redistribution support so that the first disinfecting single uniform barrier polymer membrane does not extend over the lower surface of the resilient medical patient pressure redistribution support;

disposing a support covering over and onto the second main surface of the releasably secured first disinfecting single uniform barrier polymer membrane on the resilient medical patient pressure redistribution support;

wherein the disinfecting single uniform barrier polymer membrane having the anti-microbial disinfectant is efficacious in the killing of pathogens associated with causing healthcare-associated infections;

wherein the disinfecting membrane comprises a thickness operable to maintain the weight distribution of a patient on the weight bearing upper textile surface of the resilient medical patient pressure redistribution support substantially the same compared to the weight distribution of the patient on the weight bearing upper textile surface of the resilient medical patient pressure redistribution support without the disinfecting membrane;

wherein the disinfecting single uniform barrier polymer membrane having the anti-microbial disinfectant is operable for greater than 99% of contact inhibition;

removing the support covering from the resilient medical patient pressure redistribution support;

removing the first releasably secured disinfecting membrane from the resilient medical patient pressure redistribution support;

inspecting the resilient medical patient pressure redistribution support, and releasably securing a second disinfecting single uniform barrier polymer membrane with static electricity in position over the weight bearing upper textile surface and along the peripherally-extending side of the resilient medical patient pressure redistribution support so that the disinfecting single uniform barrier polymer membrane does not extend over the lower surface of the resilient medical patient pressure redistribution support; and disposing a support covering over and onto the second main surface of the releasably secured disinfecting single uniform barrier polymer membrane on the resilient medical patient pressure redistribution support.

* * * * *